(12) United States Patent
Doschak et al.

(10) Patent No.: US 9,950,082 B2
(45) Date of Patent: Apr. 24, 2018

(54) PREPARATION OF BONE-SEEKING SUPERPARAMAGNETIC IRON NANOPARTICLES AS CONTRAST AGENTS AND METHODS FOR USING THE SAME

(71) Applicant: THE GOVERNORS OF THE UNIVERSITY OF ALBERTA, Edmonton (CA)

(72) Inventors: Michael Doschak, Edmonton (CA); Arash Panahifar, Edmonton (CA); Morteza Mahmoudi, Tehran (IR)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

(21) Appl. No.: 14/781,664

(22) PCT Filed: Apr. 1, 2014

(86) PCT No.: PCT/IB2014/001677
§ 371 (c)(1),
(2) Date: Oct. 1, 2015

(87) PCT Pub. No.: WO2014/184670
PCT Pub. Date: Nov. 20, 2014

(65) Prior Publication Data
US 2016/0058892 A1 Mar. 3, 2016

Related U.S. Application Data

(60) Provisional application No. 61/808,401, filed on Apr. 4, 2013.

(51) Int. Cl.
A61K 9/00 (2006.01)
A61K 49/18 (2006.01)
A61K 49/10 (2006.01)

(52) U.S. Cl.
CPC .......... *A61K 49/1842* (2013.01); *A61K 49/10* (2013.01)

(58) Field of Classification Search
None
See application file for complete search history.

(56) References Cited

U.S. PATENT DOCUMENTS 8,334,320 B2 * 12/2012 Liu .................. A61K 31/195
514/262.1
2009/0311237 A1 * 12/2009 Frost ................ A61K 9/0019
424/94.62
2010/0272653 A1 10/2010 Greb et al.

OTHER PUBLICATIONS

Portet et al, Comparative Biodistribution of Thin-Coated Iron Oxide Nanoparticles TCION: Effect of Different Bisphosphonate Coatings, Drug Development Research, 2001, 54, 173-181.*

(Continued)

*Primary Examiner* — Paul W Dickinson
(74) *Attorney, Agent, or Firm* — Gardner Groff Greenwald & Villanueva, PC

(57) ABSTRACT

Described herein are compositions having a nanoparticle that is conjugated to at least one bone targeting moiety, wherein the bone targeting moiety is bonded to the nanoparticle by a linker, wherein the nanoparticle contains iron, and wherein the compositions are neutral or pharmaceutically acceptable salts or esters. Also described herein are methods of making these compositions. In one aspect, the nanoparticles serve as contrast agents for magnetic resonance imaging of bone metabolism. The compounds, compositions, and methods described herein can be used in a number of therapeutic applications including diagnosing or monitoring fracture and/or the progress of conditions associated with bone loss, which include, but are not limited to, osteoporosis, Paget's disease, osteolytic tumors, rheumatoid (Continued)

arthritis, psoriatic arthritis, ankylosing spondylitis, osteoarthritis, osteopenia, and hypercalcemia.

23 Claims, 10 Drawing Sheets

(56) References Cited

OTHER PUBLICATIONS

Extended European Search Report for 14798291.2 dated Nov. 11, 2016.
Benyettou, F. et al., "Superparamagnetic nanovector with anti-cancer properties: (gamma) Fe2O3@Zoledronate," (2009), Int. J. Pharmaceutics, 379:324-327.
Lalatonne, Y. et al., "Superparamagnetic bifunctional bisphosphonates nanoparticles: a potential MRI contrast agent for osteoporosis therapy and diagnostic," (2010), J. Osteoporosis, vol. 2010, Article ID 747852, 7 pages.
Chen, T-J et al. "Targeted folic acid-PEG nanoparticles for noninvasive imaging of folate receptor by MRI;" Journal of Biomedical Materials Research Part A; 2008; 87A(1):165-175.
Panahifar, A. et al. "Synthesis and in Vitro Evaluation of Bone-Seeking Superparamagnetic Iron Oxide Nanoparticles as Contrast Agents for Imaging Bone Metabolic Activity;" ACS Applied Materials and Interfaces; 2013; 5:5219-5226.
Zayed, G.M.S. et al. "Heterobifunctional Poly(ethylene glycol) Derivatives for the Surface Modification of Gold Nanoparticles Toward Bone Mineral Targeting;" Macromolecular Bioscience; 2012; 12:1124-1136.
International Search Report and Written Opinion for PCT/IB2014/001677 dated Jan. 2, 2015.

\* cited by examiner

PREPARATION OF BONE-SEEKING SUPERPARAMAGNETIC IRON NANOPARTICLES AS CONTRAST AGENTS AND METHODS FOR USING THE SAME

CROSS REFERENCE TO RELATED APPLICATIONS

This application claims priority upon U.S. provisional application Ser. No. 61/808,401, filed Apr. 4, 2013. This application is hereby incorporated by reference in its entirety for all of its teachings.

BACKGROUND

Bone disorders such as osteoarthritis (OA) and osteoporosis are responsible for a large global economic burden. OA alone affects approximately 27 million adults in the United States. OA is a chronic condition that is usually diagnosed at a late stage when the only treatment options are total joint replacement surgery or palliative treatments. Regardless of whether the cause of OA is cartilage, bone, or both, early diagnosis is of vital importance in planning treatment. Meanwhile, osteoporosis affects 44 million people age 50 or older in the United States alone. Other conditions including, but not limited to, bone fracture, Paget's disease, osteolytic tumors, rheumatoid arthritis, psoriatic arthritis, ankylosing spondylitis, osteopenia (including drug-induced osteopenia), and hypercalcemia, also cause loss of bone mass and affect hundreds of millions of people worldwide.

Those suffering from these maladies are predisposed to loss of bone mass, enhanced bone fragility, and increased risk of traumatic fracture. Each condition has various etiologies such as congenital conditions, malnutrition, or risk of various additional factors. For example, osteoporosis alone has at least three etiologies. In all types, the declining ability of the bone remodeling machinery results in bone fragility. Type I or postmenopausal osteoporosis occurs in women 51-75 years of age; in this type, estrogen deficiency shifts bone remodeling to favor bone resorption over bone formation, resulting a net bone loss. Type II or senile osteoporosis affects women about twice as often as it affects men and occurs from ages 75 to 90 years. Type III or secondary osteoporosis is caused by medications, cancers, endocrine disorders, chronic liver and/or kidney disease, and other conditions.

The current gold standard for diagnosis of OA is X-ray radiography to measure the distance between the two ends of bone in a joint as an indirect measure of cartilage loss. Nonetheless, OA is characterized by altered bone remodeling during its progression. Bone remodeling in OA patients is further characterized by occurring to different degrees at different locations in the body.

It has been suggested that changes in bone happen before cartilage degeneration begins, although this idea remains controversial. Currently, nuclear medicine is able to image bone turnover after the administration of bone-targeting tracers such as $^{99m}$Tc-MDP (methylene diphosphonate). However, radioisotope availability is sometimes limited, and exposure to radioisotopes carries with it some health risks, not only to the patient, but also to those who encounter the patient for a few days after treatment. Bone scintigraphy has been demonstrated to predict cartilage loss before the occurrence of radiographic changes. Alternatively, elemental strontium has been used as a calcium surrogate in high-resolution mapping of the metabolic activity of bone in osteoarthritic rats.

Magnetic resonance imaging (MRI) is a powerful diagnostic modality for imaging and assessment of cartilage, as well as inflammation-related features such as synovitis and bone marrow lesions, but is limited to structural information. The development of a contrast agent targeting bone would open the possibility for imaging bone metabolic activity via MRI while at the same time collecting structural information, simply by changing the pulse sequence. This could aid in diagnosis and treatment decisions for patients with a variety of metabolic bone disorders.

SUMMARY

Described herein are iron nanoparticles that are conjugated to at least one bone targeting moiety, wherein the bone targeting moiety is bonded to the nanoparticle by a linker, and wherein the compositions are neutral or pharmaceutically acceptable salts or esters. Also described herein are methods of making these compositions. In one aspect, the nanoparticles serve as contrast agents for magnetic resonance imaging of bone metabolism. The compounds, compositions, and methods described herein can be used in a number of therapeutic applications including diagnosing or monitoring the progress of conditions associated with fracture and/or bone loss, which include, but are not limited to, osteoporosis, Paget's disease, osteolytic tumors, rheumatoid arthritis, psoriatic arthritis, ankylosing spondylitis, osteoarthritis, osteopenia, and hypercalcemia.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
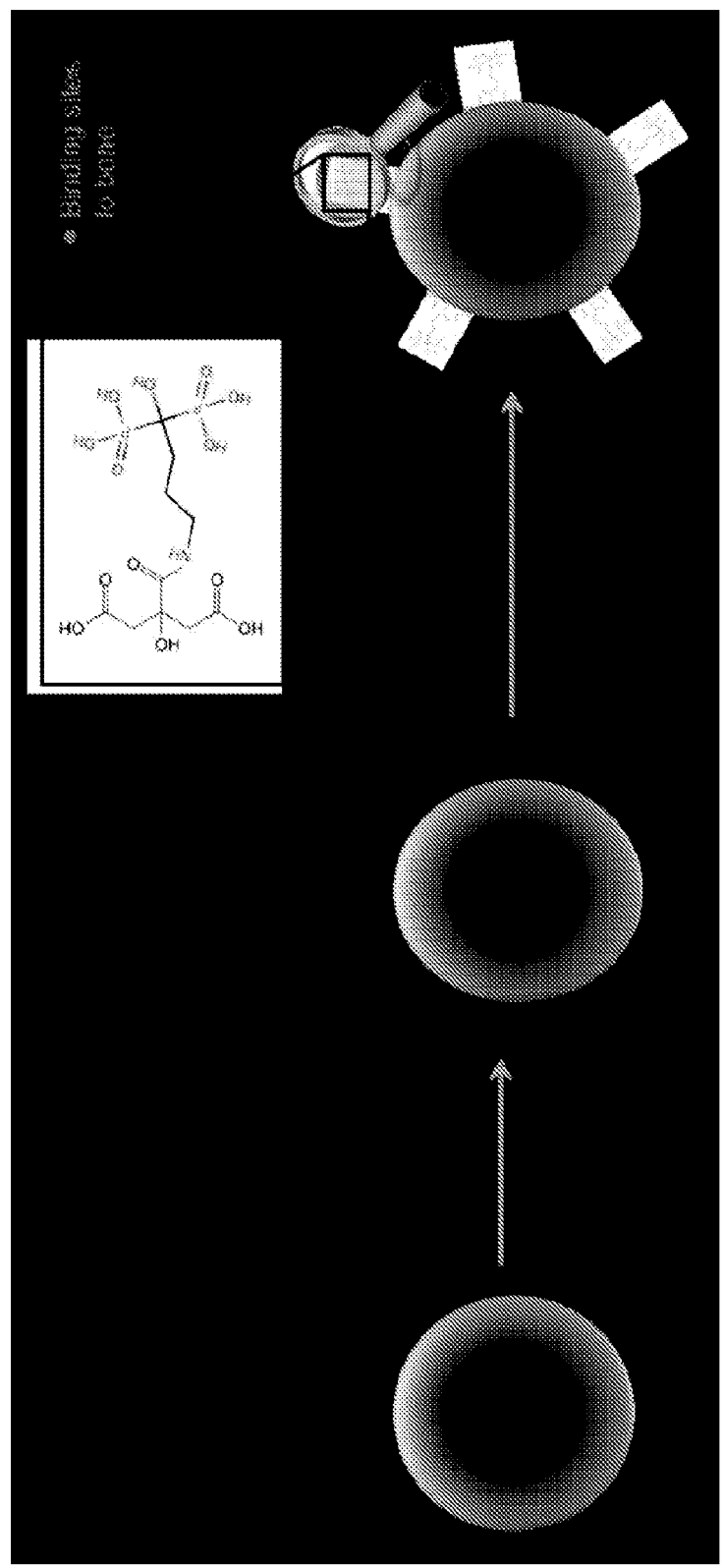
FIG. 1 shows an overview of the process of conjugating a bisphosphonate to an iron-containing nanoparticle.

Before the present compounds, compositions, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a bisphosphonate" includes mixtures of two or more such bisphosphonates, and the like.

"Optional" or "optionally" means that the subsequently described event or circumstance can or cannot occur, and that the description includes instances where the event or circumstance occurs and instances where it does not. For example, the phrase "optionally administered intravenously to a subject" means that the compositions described herein can or cannot be administered to a subject via an IV line.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Subject" refers to animals including, but not limited to, mammals such as humans, non-human primates, sheep, dogs, rodents (e.g., mouse, rat, guinea pig, etc.), cats, rabbits, cows, and to non-mammals including, but not limited to, chickens, amphibians, and reptiles, any of whom are at risk for or have been diagnosed with a condition that causes bone loss.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, a targeting moiety that contains at least one —NH group can be represented by the formula Y—NH, where Y is the remainder (i.e., residue) of the targeting moiety.

The term "linker" refers to a chemical group that is capable of covalently linking the iron nanoparticles described herein to a bone targeting moiety such as the bone targeting moieties described herein. Structural information regarding the linkers used herein is provided below.

"Bone targeting moiety" refers to any chemical compound that has an affinity for bone mineral, matrix, and/or cells, including bone hydroxyapatite, osteocytes, osteoblasts, osteoclasts, or any combination thereof, and is capable of selectively targeting bone mineral, matrix, and/or cells including hydroxyapatite, osteocytes, osteoblasts, osteoclasts, or any combination thereof, over other cells and tissues. Structural information regarding the bone targeting moieties used herein is provided below.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl, and the like. A "lower alkyl" group is an alkyl group containing from one to six carbon atoms.

The term "alkylene group" as used herein is a branched or unbranched unsaturated hydrocarbon group of 1 to 24 carbon atoms such as methylene, ethylene, propene, butylene, isobutylene, and the like.

The term "cycloalkyl group" as used herein is a non-aromatic, carbon-based ring composed of at least three carbon atoms. Examples of cycloalkyl groups include, but are not limited to, cyclopropyl, cyclobutyl, cyclopentyl, cyclohexyl, etc. The term "heterocycloalkylgroup" is a cycloalkyl group as defined above where at least one of the carbon atoms of the ring is substituted with a heteroatom such as, but not limited to, nitrogen, oxygen, sulfur, of phosphorus.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, halo, hydroxy, alkylthio, arylthio, alkoxy, aryloxy, amino, mono- or di-substituted amino, ammonio or substituted ammonio, nitroso, cyano, sulfonato, mercapto, nitro, oxo, alkyl, alkenyl, cycloalkyl, benzyl, phenyl, substituted benzyl, substituted phenyl, benzylcarbonyl, phenylcarbonyl, saccharides, substituted benzylcarbonyl, substituted phenylcarbonyl, and phosphorus derivatives. The aryl group can include two or more fused rings, where at least one of the rings is an aromatic ring. Examples include naphthalene, anthracene, and other fused aromatic compounds.

The term "alkyl amine" as used herein can refer to the general formula —N(R)H wherein R includes an alkyl group as defined above.

The term "alkylene amine" as used herein can refer to the general formula —N(R)H wherein R includes an alkylene group as defined above.

The term "aryl amine" as used herein can refer to the general formula —N(R)H wherein R includes an aryl group as defined above.

The term "amino group" as used herein can refer to the general formula —$NH_2$.

The term "carboxylate" as used herein can refer to the general formula —COOR, where R includes hydrogen, an alkyl or aryl group as defined above (i.e., an ester), or a counterion such as $Na^+$ (i.e., a salt).

A "contrast agent" as used herein is any substance that can assist in improving the visibility of body structures using a medical imaging technique such as "magnetic resonance imaging" (also known as MRI). In one aspect, an MRI contrast agent alters the relaxation time of atoms within a particular type of body tissue, after the segment of the body containing the tissue is exposed to a strong magnetic field and a radio frequency (RF) pulse is applied. In a further aspect, this pulse causes nuclei to spin; eventually, the nuclei relax and this relaxation may be aided by a contrast agent. In a further aspect, this relaxation emits energy which can be mathematically converted to an image by a computer.

"Pharmaceutical" as used herein refers to any chemical compound or composition used in the diagnosis, treatment, or prevention of disease. In one aspect, the pharmaceutical compositions described herein are used for diagnosis of disease. In another aspect, the pharmaceutical compositions are used to monitor the progress of an already-diagnosed disease or condition.

"SPIONs" as used herein are superparamagnetic iron oxide nanoparticles. Methods for preparing SPIONs are described below. Superparamagnetism is the state when a nanoparticle is below a certain size and can be magnetized when placed in magnetic field.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly-recited values of about 1 to about 5, but also to include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. The same principle applies to ranges reciting only one numerical value as a minimum or a maximum. Furthermore, such an interpretation should apply regardless of the breadth of the range or the characteristics being described.

I. Compositions

Described herein are compositions having at least one bone targeting moiety, wherein the targeting moiety is bonded to an iron nanoparticle by a linker and wherein the compositions are neutral or pharmaceutically acceptable salts or esters. Each component used to prepare the nanoparticles described herein and methods for preparing the same are described in detail below.

a. Iron Nanoparticles

Iron oxide nanoparticles are used herein as precursors to the final nanoparticle compositions. In one aspect, the iron is present in the form of $Fe_3O_4$ and $\gamma$-$Fe_2O_3$. In one aspect, the iron nanoparticle can be a hybrid particle. For example, the nanoparticle can have a core composed of one or more other metals (e.g., silver or gold) and an outer shell composed of an iron oxide. Alternatively, the core can be composed of one or more iron oxides and the outer shell can be composed of one or more other metals. Thus, in certain aspects, the iron nanoparticles useful herein can be composed of 100% iron oxide(s) or less than 100%, where the iron oxide forms an outer shell of the nanoparticle.

In one further aspect, the nanoparticles are superparamagnetic. In a further aspect, the iron-containing nanoparticles are synthesized by a microemulsion technique. In one aspect, the microemulsion technique involves mixing two microemulsions, wherein the first microemulsion contains an oil phase and an aqueous solution of iron (II) and iron (III) chloride and the second microemulsion contains an oil phase and an aqueous solution of a reducing agent. In one aspect, the oil phase is composed of toluene. In another aspect, the reducing agent is concentrated ammonium hydroxide. In some aspects, both microemulsions contain a surfactant. In one aspect, the surfactant is cetyltrimethylammonium bromide (CTAB). In some aspects, the microemulsions are mixed while also being titrated with 1-butanol. In one aspect, 1-butanol is a co-surfactant which can help form microemulsions. In certain aspects, the microemulsion technique ensures that SPIONs will be produced which are water dispersible and which have a narrow size distribution. In this aspect, the properties of the SPIONs produced are particularly useful in biological applications. Exemplary procedures for making SPIONs are provided in the Examples.

In a further aspect, the microemulsions can be mixed to form $Fe_3O_4$ nanoparticles. In some aspects, sonication is applied during mixing to prevent aggregation of nanoparticles. In some aspects, the nanoparticles are purified by removal from solution with a magnet, followed by washing with one or more solvents. In one aspect, the solvents include ethanol, acetone, water, or combinations thereof. In certain aspects, the nanoparticles are known as superparamagnetic iron oxide nanoparticles, or SPIONs.

In one aspect, all steps for the preparation of the iron nanoparticles synthesis are carried out under an inert atmosphere. In a further aspect, the inert atmosphere is nitrogen gas.

In some aspects, the iron concentration in the SPIONs can be measured by dissolution of SPION suspensions in nitric acid, followed by analysis using atomic absorption spectroscopy or any another technique for metal analysis known in the art.

In one aspect, following synthesis, the SPIONs can be conjugated to a linker. The linker herein can be hydrophilic, hydrophobic, or amphiphilic. In one aspect, the linker is water-soluble. In some aspects, the linkers described herein have at least one, at least two, or at least three functional groups capable of covalent bonding. In some aspects, the linkers have at least two functional groups, one of which is capable of chemisorbing to an iron-containing nanoparticle and the other of which is capable of reacting with the bone targeting moiety. In other aspects, the linkers have at least three functional groups, two of which chemisorb to an iron-containing nanoparticle and the other of which reacts with the bone targeting moiety. In one aspect, the functional groups are identical. In certain aspects, the functional groups include carboxylic acids. In one aspect, the linker is a dicarboxylic acid. In another aspect, the linker is a tricarboxylic acid. In a further aspect, the tricarboxylic acid is citric acid.

b. Linkers

The iron nanoparticles have a linker bound to the iron particle. In one aspect, the SPIONs are conjugated to the linker by mixing. In one aspect, this mixing occurs at room temperature. In another aspect, this mixing occurs for 1 h, 2 h, 3 h, 4 h, 5 h, or 6 h. In a further aspect, one or more of the functional groups on the linker chemisorb to the SPIONs. In an additional aspect, the chemisorption process can also involve an ion exchange process.

In one aspect, the linker has one or more carboxylate groups. In another aspect, the linker has two, three, four, or five carboxylate groups. An example of a useful linker herein possessing a plurality of carboxylate groups is citric acid. In one aspect, surface hydroxyl groups on the SPIONs are exchanged for carboxylic acid groups from the linker, thus bonding the linker to the SPIONs.

In another aspect, the linker is a fatty acid such as, for example, oleic acid, linked to a phospholipid possessing a hydrophilic group such as PL-PEG-COOH. In this aspect, the bare iron nanoparticles are coated with oleic acid, followed by coating with PL-PEG-COOH. After this step, the functionalized nanoparticles possess COOH functional groups that can covalently bind to a bone targeting compound possessing a nucleophilic group (e.g., —NH$_2$). In one aspect, the iron nanoparticles would have prolonged blood circulation due to the hydrophilic PEG group.

In one aspect, the weight ratio of SPIONs to linker can be from 2:1 to 10:1; 2:1 to 9:1; 3:1 to 9:1; 5:1 to 9:1, or about 8:1. In some aspects, the solutions of SPIONs and/or linker are pH adjusted prior to mixing with one another. In a further aspect, the solution of SPIONs is acidified by adding HCl prior to the addition of linker. In another aspect, the solution pH is adjusted to about 2, about 2.5, about 3, about 3.5, about 4, or about 4.5. In a still further aspect, the SPIONs conjugated to linker (SPIONs-COOH) are purified by magnetic separation.

Depending upon the selection of the bone targeting moiety, it is desirable to ensure the iron nanoparticle is sufficiently coated with the linker prior to attachment of the bone targeting moiety. For example, phosphonate groups in a bone targeting compound can form strong complexes with iron structures. Therefore, for successful targeting of bone it is desirable to prevent phosphonate groups of bisphosphonates from binding onto the surface of the iron nanoparticles. The starting materials and methods for making the iron nanoparticles described herein prevent this, which preserves the active phosphonate groups for targeting bone.

In one aspect, when the iron nanoparticle has a bound linker with free carboxylate groups, the carboxylate group can be activated prior to conjugation to the bone targeting moiety. This can be done by any technique for activation of a functional group known in the art. Skilled artisans will be able to determine the best activation protocol for a particular functional group. In one aspect, the activation employs 1-ethyl-3-(3-dimethylaminopropyl)carbodiimide (EDC) and N-hydroxysuccinimide (NHS). In this aspect, the subsequent reaction with an amine occurs more quickly than if the carboxylate functional group is not activated with EDC and NHS. In one aspect, a solution containing EDC and NHS is mixed with a suspension of SPIONs-COOH. In a further aspect, this mixing occurs at room temperature. In an additional aspect, the mixing occurs for 10 min, 20 min, 30 min, 40 min, 50 min, or 1 h. In another aspect, this mixing occurs in a buffer solution. In one aspect, the buffer is a phosphate buffer. In another aspect, the buffer is MES buffer. The buffer holds the reaction solution at a particular pH. In one aspect, the pH is about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In another aspect, the iron nanoparticle with activated carboxylate group(s) can be purified prior to conjugation to a bone targeting moiety. In one aspect, the purification is achieved by performing dialysis.

c. Targeting Moiety

The iron nanoparticles with bound linker intermediate as described herein can be reacted with a bone targeting moiety to form compounds having at least one nanoparticle conjugated to at least one bone targeting moiety. The compositions described herein can include a bone targeting compound, wherein the bone targeting compound can include a bisphosphonate containing compound.

Bisphosphonates have a strong affinity for bone, which makes them effective therapeutic agents for metabolic bone disorders. Without wishing to be bound by theory, the main mechanism by which bisphosphonates have been hypothesized to target bone is related to their PCP backbones coupled with contributions from R$^1$ hydroxyl groups. Nitrogen-containing bisphosphonates can also form hydrogen bonds with hydroxyapatite (HA) crystals in some instances. Bisphosphonates are the first-line option for treatment of metabolic bone diseases characterized by excessive bone resorption such as osteoporosis or Paget's disease. Bisphosphonates inhibit osteoclast-mediated bone resorption, thus returning bone metabolism to homeostasis.

In one aspect, the bone targeting moiety is a bisphosphonate having the formula I:

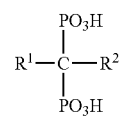

I wherein R$^1$ and R$^2$ are, independently, hydrogen, a hydroxyl group, an alkyl group, an alkylene group, an amine group, a thiol group, an aryl group, or any combination thereof, or the pharmaceutically salt or ester thereof, and wherein R$^1$ or R$^2$ is covalently attached to the linker. In the case when the iron nanoparticle with bound linker has a free carboxylate group, a bone targeting compound possessing a nucleophilic group such as an amino group (substituted or unsubstituted), a hydroxyl group, or a thiol group, can be used to covalently attach the bone targeting compound to the linker. In one aspect, R$^1$ is a hydroxyl group and R$^2$ is an alkyl amine group —NHR, where R is a branched or linear alkyl group. For example, R can be —(CH$_2$)$_n$—, where n is from 1 to 10.

In some aspects, the bone targeting moiety includes an amino group. In some aspects, the amino group is a primary amine. In a further aspect, the amino group is an alkyl amine connected to an alkyl chain having from 1 to 10 carbon atoms. In a still further aspect, the alkyl chain has from 2 to 6 carbon atoms. In yet another aspect, the alkyl chain has 4 carbon atoms. In another aspect, if at least one amino group is present, the linker can covalently bond to the bone targeting moiety. In a further aspect, $R^1$ in formula I is a hydroxyl group and $R^2$ is an alkyl amine group —NHR, where R is a branched or linear alkyl group. For example, R can be —$(CH_2)_n$—, where n is from 1 to 10.

In one aspect, the bisphosphonate containing compound that is reacted with the iron nanoparticle with bound linker possessing free carboxylate groups includes, but is not limited to, a residue of etidronic acid, clodronic acid, tiludronic acid, pamidronic acid, neridronic acid, olpadronic acid, alendronic acid, ibandronic acid, zolendronic acid, risedronic acid, or a combination thereof. In some aspects, the bisphosphonate containing compound is a residue of [4-amino-1-hydroxy-1-(hydroxy-oxido-phosphoryl)-butyl] phosphonic acid. In this aspect, the targeting moiety is covalently attached to the linker via an amide bond involving the nitrogen atom of the targeting moiety's alkyl amino group.

II. Preparation of Iron Nanoparticles

Further described herein are methods of making the compositions having a nanoparticle linked to a bone targeting moiety. In one aspect, the method involves:
  a. reacting at least one iron nanoparticle with at least one linker comprising a carboxylate group to form a first nanoparticle, wherein the linker is bound to the iron nanoparticle and the bound linker comprises at least one unreacted carboxylate group;
  b. reacting the first nanoparticle with a bisphosphonate compound, wherein the bisphosphonate compound has a carboxylate-reactive group to produce the iron nanoparticle.

The method generally involves chemisorbing at least one functional group such as, for example, a carboxylic acid, present in a linker, to an iron-containing nanoparticle, to form a functionalized nanoparticle intermediate, and reacting the functionalized nanoparticle intermediate with a bisphosphonate containing compound. A non-limiting procedure is depicted in FIG. 1. The functionalized nanoparticle intermediate can optionally be activated by techniques known in the art such as, for example, EDC/NHS activation. In this method, any combination of nanoparticles, linkers, and bone targeting moieties described above can be used. In this method, the bone targeting moiety can include any of the bisphosphonate compounds described above. For example, the bisphosphonate compound can include an amine containing bisphosphonate compound.

The amount of linker used relative to the nanoparticle will determine the number of linkers attached to the nanoparticle. A particular ratio, for example, a weight/weight ratio, of the nanoparticle to linker can be used to form a nanoparticle-linker intermediate. In addition, reaction times can be adjusted to form various nanoparticle-linker intermediates with varying degrees of surface coverage of linker on nanoparticle. In one aspect, the entire surface of the nanoparticle is covered with linker molecules. In one aspect, the ratio of the nanoparticle linker can include, but is not limited to, a 10:1, an 8:1, a 6:1, or a 4:1 weight/weight ratio. In certain aspects, the ratio of the nanoparticle to linker is an 8:1 weight/weight ratio. In some aspects, the peptide sequence and linker are reacted for a period of time including, but not limited to, 30 min, 1 h, 1.5 h, 2 h, 2.5 h, 3 h, 3.5 h, 4 h, 4.5 h, or 5 h at about room temperature to form the nanoparticle-linker intermediate.

In some aspects, when the nanoparticles and linker are reacted, organic solvents, organic solvents mixed with aqueous solvents including buffers, or any combination thereof, can be added. Organic solvents can include, but are not limited to, dimethyl sulfoxide (DMSO), dimethylformamide (DMF), chloroform, triethylamine (TEA), and alcohols. Aqueous solvents and buffers can include, but are not limited to, water, phosphate buffers, carbonate buffers, MES buffers, acetate buffers, and the like, and combinations thereof. In one aspect, phosphate buffer is used.

In some aspects, either when reacting the nanoparticles and linkers (i.e. during the formation of the nanoparticle-linker intermediate) or after the formation of the nanoparticle-linker intermediate, the pH can be adjusted. In some aspects, the pH should be acidic, wherein the pH ranges from 2.0 to 6.0, from 2.0 to 4.0, or can be about 3.0. In certain aspects, dilute HCl can be added to adjust the pH. In one aspect, 0.1 M HCl is added to the nanoparticle suspension to adjust the pH.

After the formation of the nanoparticle-linker intermediates (SPIONs-COOH), the intermediate can optionally be activated by a technique known in the art. Skilled artisans will be able to determine the best activation protocol for a particular functional group. In one aspect, the activation employs 1-ethyl-3-(3-dimethylaminopropyl)carbodiimide (EDC) and N-hydroxysuccinimide (NHS). In one aspect, a solution containing EDC and NHS is mixed with a suspension of SPIONs-COOH. In a further aspect, this mixing occurs at room temperature. In an additional aspect, the mixing occurs for 10 min, 20 min, 30 min, 40 min, 50 min, or 1 h. In another aspect, this mixing occurs in a buffer solution. In one aspect, the buffer is a phosphate buffer. In another aspect, the buffer is MES buffer. The buffer holds the reaction solution at a particular pH. In one aspect, the pH is about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In another aspect, the activated SPIONs-COOH (SPIONs-Active) are stable and can be purified prior to conjugation to a bone targeting moiety. In one aspect, the purification is achieved by performing dialysis.

In one aspect, after formation of the iron nanoparticle with bound linker can be reacted with a bone targeting compound described herein in order to form the compositions described herein. In some aspects, a particular ratio, for example a weight/weight ratio, of iron nanoparticle-linker to bone targeting moiety can be utilized to form the compositions described herein. In one aspect, the bone targeting moiety is also used as a pharmaceutical treatment of metabolic bone diseases, where the amount of bone targeting moiety can be selected to match a typical therapeutic dosage of bone targeting moiety such as would be administered by a physician. Such dosages and methods for determining them are known to those skilled in the art of treating metabolic bone diseases.

In some aspects, the pH can be adjusted during and/or after the reaction. In some aspects, buffers including, but not limited to, phosphate buffers, MES buffers, acetate buffers, citrate buffers, or a combination thereof, can be added. In some aspects, the pH can be adjusted to a pH ranging from 6.0 to 8.5, from 6.5 to 7.5, or from 7.0 to 7.5. In some aspects, the pH can be adjusted to 7.2. In further aspects, a salt such as sodium chloride can be added to a suspension of iron nanoparticles at a concentration of from about 10 mM to 300 mM, or from about 50 mM to 200 mM, or about 150 mM.

In certain aspects, analytical techniques such as atomic absorption spectroscopy, transmission electron microscopy, atomic force microscopy, dynamic light scattering, Fourier-transform infrared spectroscopy, and x-ray photoelectron spectroscopy can be used to characterize the iron nanoparticles produced herein at various points during synthesis.

Additional, non-limiting procedures for making the compositions described herein are provided in the Examples section and in the drawings.

Any of the compounds described herein can be pharmaceutically-acceptable salts or esters thereof. In one aspect, pharmaceutically-acceptable salts are prepared by treating the free acid with an appropriate amount of a pharmaceutically-acceptable base. Representative pharmaceutically-acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, or the like. In one aspect, the reaction is conducted in water, alone or in combination with an inert, water-miscible organic solvent, at a temperature of from about 0° C. to about 100° C., such as at room temperature. In certain aspects where applicable, the molar ratio of the compounds described herein to base used is chosen to provide the ratio desired for any particular salt. For preparing, for example, the ammonium salts of the free acid starting material, the starting material can be treated with approximately one equivalent of a pharmaceutically-acceptable base to yield a neutral salt.

In another aspect, if the compound possesses a basic group, it can be protonated with an acid such as, for example, HCl, HBr, or $H_2SO_4$, to produce the cationic salt. In one aspect, the reaction of the compound with the acid or base is conducted in water, alone or in combination with an inert, water-miscible organic solvent, at a temperature of from about 0° C. to about 100° C., such as at room temperature. In certain aspects where applicable, the molar ratio of the compounds described herein to acid used is chosen to provide the ratio desired for any particular salts. For preparing, for example, the hydrochloride salts of the free base starting material, the starting material can be treated with approximately one equivalent of a pharmaceutically-acceptable acid to yield a neutral salt.

Ester derivatives are typically prepared as precursors to the acid forms of the compounds. Generally, these derivatives will be lower alkyl esters such as methyl, ethyl, and the like. Amide derivatives —(CO)NH$_2$, —(CO)NHR, and —(CO)NR$_2$, where R is an alkyl group defined above, can be prepared by reaction of a carboxylic acid containing compound with ammonia or a substituted amine.

In a further aspect, the nanoparticles, linkers, and bone targeting moieties mentioned above can be used to make contrast agents for magnetic resonance imaging (MRI). In one aspect, the contrast agents are administered as, or as part of, pharmaceutical compositions. The complexes described above can be administered to a subject using techniques known in the art. For example, pharmaceutical compositions can be prepared with the complexes. It will be appreciated that the actual preferred amounts of the complex in a specified case will vary according to the specific compound being utilized, the particular compositions formulated, the mode of application, and the particular situs and subject being diagnosed or imaged. Physicians and formulators skilled in the art of determining doses of pharmaceutical compounds will have no problems determining doses according to standard recommendations.

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, and Tris buffer, while examples of preservatives include thimerosal, cresols, formalin, and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents, and the like, in addition to the molecule of choice.

The pharmaceutical composition can be administered in a number of ways depending on whether local or systemic imaging is desired and on the area to be treated. Administration can be intravenous or intraperitoneal, or the pharmaceutical composition can be injected directly into a subject's joint.

Preparations for administration include sterile aqueous or non-aqueous solutions, suspensions, and emulsions. Examples of non-aqueous carriers include water, alcoholic/aqueous solutions, emulsions, or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, inert gases, and the like.

III. Applications of Iron Nanoparticles

In some aspects, the compositions described herein can be administered to a subject as a contrast agent prior to imaging the subject using magnetic resonance imaging. In certain aspects, the subject has been diagnosed with a metabolic bone disorder. In other aspects, the subject is believed to be at risk of developing a metabolic bone disorder due to risk factors such as age, diet, cancer, infection, family history, postmenopausal status, or the like, or a combination thereof. In one aspect, the subject believed to be at risk has not yet been diagnosed with a metabolic bone disorder. In a further aspect, use and/or practice of the compounds, compositions, and methods described herein can be used to diagnose a metabolic bone disorder in a subject. In one aspect, the compounds, compositions, and methods described herein can be used to confirm a diagnosis of a metabolic bone disorder in a subject in conjunction with tests and information such as, for example, bone density testing, genetic tests, a subject's medical history, and/or the subject's family medical history. In a still further aspect, the compounds, compositions, and methods described herein can be used to monitor the progress of an already-diagnosed metabolic bone disorder.

In certain aspects, the condition may be linked to congenital conditions or improper diet. In this aspect, an osteoclast may remove bone tissue (i.e., bone resorption) more quickly than new bone cells and tissue can be produced. The overall effect leads to osteoclast mediated resorptive bone loss. In some aspects, the condition includes, but is not limited to, osteoporosis, Paget's disease, osteolytic tumors, rheumatoid arthritis, psoriatic arthritis, ankylosing spondylitis, osteoarthritis, hypercalcemia, osteopenia including drug induced osteopenia, and/or bone fracture, or a combination thereof. In some aspects, the condition causes osteoclast mediated resorptive bone loss.

In some aspects, bone metabolism can be imaged by contacting the bone with the compositions described herein. In this aspect, the nanoparticles are superparamagnetic and serve as contrast agents for magnetic resonance imaging, while the conjugated bone-targeting moieties ensure that the contrast agents will be localized at bone-containing sites in the body. In each of these aspects, administration may be via injection including intramuscular, intravenous, or subcutaneous injection.

In one aspect, a method for imaging a bone metabolism in a subject comprising:

a. administering an iron nanoparticle described herein to a subject; and b. imaging the bone by magnetic resonance imaging.

In one aspect, the route of administration would be intravenous injection (i.e. IV). A suspension of bone-targeting iron nanoparticles can be injected into the patient and after the optimal duration, the bone of interest is imaged by MRI. The imaging can be performed in T2 mode or T1 mode. Alternatively, imaging is possible in gradient weighted mode in order to visualize the altered local magnetic signal due to the nanoparticles. The nanoparticles described herein reduce relaxation times in the affected area, mainly T2 value but also T1 value. The images that are produced can be subsequently evaluated in order to assess the state of the bone.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such process conditions.

Materials and Methods

1. Materials $FeCl_2$.tetra-hydrate (≥99%), $FeCl_3$.hexa-hydrate (≥99%), 1-Butanol (≥99%), EDC (N-Ethyl-N'-[3(dimethylamino)propyl]carbodiimide hydrochloride), citric acid (≥99%) and nitric acid (70%) were purchased from Sigma-Aldrich (USA). Alendronate sodium tri-hydrate (≥97%) and CTAB (Hexadecyltrimethylammonium bromide, ≥99%) were purchased from Sigma (USA). NHS (N-hydroxysuccinimide, ≥98%) was from Aldrich (Germany), ammonium hydroxide solution (25%) was from Fluka (Switzerland), Toluene was from Caledon (Canada), acetone and ethanol were purchased from Fisher scientific (USA). Hydroxyapatite powder (Type II, particle size of 20 μm) was purchased from Bio-rad (USA) and used for bone affinity tests. Dialysis bag (2000 MWCO) was purchased from Spectrum Laboratories (USA).

The following equipment were used in the synthesis and characterization experiments: ultrasonic probe (Sonicator W-375, Heat systems Ultrasonics, USA), homogenizer (Bio-homogenizer 1281, Biospec, USA), Atomic Force Microscope (AFM) (BioScope Catalyst, Bruker, USA), Atomic Absorption Spectrometer (Spectra AA 880, Varian, Australia). The FT-IR spectra were recorded on KBr pellets using Nicolet Magna-IR 550 spectrometer (Thermo Scientific, USA). The samples for Transmission Electron Microscopy (TEM) were prepared by placing a drop of suspension on a cupper-coated grid and removing the excess solution with filter paper and the imaging was performed at 80 KV using Morgagni (Philips/FEI, USA). Dynamic light scattering (DLS) measurements were performed using Nano-ZS 3600 instrument (Malvern, UK). For X-ray Photoelectron Spectroscopy (XPS), samples in powder form were submitted for analysis using AXIS Ultra XPS imaging spectrometer (Kratos analytical, Japan). X-ray radiograph of SPIONs targeted to HA powder was captured using Skyscan 1176 in-vivo micro-CT (SkyScan, Belgium). All glasswares used in synthesis were washed with 10% $HNO_3$ prior to use.

2. Synthesis of SPIONs

In order to obtain size-controlled nanoparticles with good hydrophilicity a water-in-oil reversed microemulsion method was employed to synthesis SPIONs. Briefly, two microemulsions (micro-A and B) with the following compositions were prepared: micro-A was composed of toluene (29 mL) as oil phase and aqueous solution of $FeCl_3$ (202 mg) and $FeCl_2$ (75 mg) at molar ratio of 2:1 in 2.045 mL of deionized (DI) water; micro-B was composed of the same oil phase and 25% ammonium hydroxide solution (2.65 mL) as reducing agent and aqueous phase. In both microemulsions CTAB was used as surfactant with water to surfactant molar ratio kept at 23 by using 1.8 g of CTAB. After preparing the above reagents in different beakers, each was separately mixed by homogenizer at the speed of 7000 rpm and 1-butanol was titrated into the above compositions while mixing. Butanol played a role as co-surfactant to help the formation of microemulsions and its addition continued until the color changed from turbid to transparent which was the indication of formation of stable microemulsion.

After making the microemulsions, micro-A and micro-B were mixed in a three-necked flask using homogenizer (7000 rpm) at 50° C. and under constant flow of $N_2$ gas. In addition, ultrasonic probe was used during the synthesis in order to prevent aggregation of nanoparticles. After 60 minutes, the reaction stopped and the product was cooled down to room temperature, then 20 ml of ethanol was added to the reaction flask to break microemulsions. SPIONs were collected with a strong magnet and supernatant discarded.

SPIONs were then washed with boiling ethanol (4×) to removed excess CTAB and further purified by washing with acetone (2×) and DI water (2×). After the washing step with acetone, nanoparticles were highly well-dispersed and could not be separated with magnet in short time, therefore they were centrifuged for 10 minutes and the pellet was redispersed in 20 mL of DI water with short sonication. The DI water used in all steps was previously deoxygenated by bubbling $N_2$ through the water for 30 minutes and also passing through Watman filter paper.

Before proceeding, a 50 µl of final solution was drawn and dissolved in 3 mL of 70% nitric acid and after 2 days submitted for Atomic Absorption Spectrometry to measure the iron concentration in the sample. This synthesis method resulted in total Fe content of 40 to 45 mg in each synthesis and after all purification steps.

3. SPIONs Functionalization and Alendronate Conjugation

The bare SPIONs were modified with citric acid according to the previously reported procedure [11] to introduce surface carboxylic acid groups for covalent conjugation to amine-terminated BP, ALN. In brief, the synthesized SPIONs were redispersed in DI water at concentration of 2 mg/mL (~72% Fe content) and sonicated for 10 minutes. The pH of the solution was adjusted at 3 by addition of 0.1M HCl and citric acid at 5% molar ratio of Fe was added to the suspension (~8:1 w/w, e.g. for 2 mg SPIONs, 0.25 mg citric acid was added) for anion exchange of OH with COOH and chemisorption. The mixture was stirred on magnet for 4 h and then washed and purified by magnetic separation (3×). The modified SPIONs were dispersed in sodium phosphate buffer (PB) (pH 7.2, 50 mM) at concentration of 1 mg/mL.

The COOH-modified SPIONs were activated employing EDC/NHS strategy and used for conjugation to ALN. According to the protocol[12], 2 mg of EDC along with 1.2 mg of NHS (1:1 molar ratio) was dissolved in 0.2 mL PB buffer and quickly added to 2 mL (equal to 2 mg of SPIONs) of SPIONs-COOH suspension and mixed for 30 minutes at room temperature while using ultrasonic probe. The activated SPIONs were dialyzed (2000 MWCO) against the same buffer for 2 h to remove excess EDC and NHS to avoid any unwanted reaction with ALN in the next step.

The activated SPIONs (2 mg) were then redispersed by quick sonication and 0.7 mg of pre-dissolved ALN in the same buffer was added to the suspension and mixed gently for 3 h. Then, the suspension was dialyzed against the same buffer for 24 h with 3 changes of buffer. Dialyzing the sample for longer resulted in precipitation of SPIONs and thus was avoided.

4. Characterization

After conjugation, the SPIONs conjugated to ALN (SPIONs-ALN) were characterized by means of various analytical techniques. TEM and AFM were used to investigate size and morphology of the SPIONs before and after drug conjugation. Moreover, DLS was used after each step to record hydrodynamic size as well as zeta potential in 3 different dispersants: DI water, PB (pH 7.2, 50 mM) with absolutely zero salt and sodium phosphate buffer saline (PBS) (pH 7.2, 50 mM, 150 mM NaCl). The hydrodynamic sizes were reported based on percent number. The structural characterization in order to confirm conjugation was performed by FT-IR to investigate functional groups and formed bonds, and XPS for surface elemental analysis. Approximately 1 mg of sample was first lyophilized for XPS and FT-IR experiments.

5. Bone Mineral Affinity Study

In order to evaluate the affinity of SPIONs-ALN towards bone, their binding to HA microparticles (average diameter of 20 µm) as the main mineral of bone were assessed in different solutions. Typically, 1.5 mL of PB (pH 7.4, 50 mM) containing approximately 50 µg of SPIONs-ALN or unmodified SPIONs was incubated with 10 mg of HA powder at dark and gently shaken. After 2 h, the supernatant containing unbound nanoparticles was removed by centrifugation at 600 rpm (1 minute). The sediment was washed 7 times with 0.2 mL buffer and each time the supernatant was removed and added to the previously collected supernatant. The sediment contained the bound nanoparticles to HA powder. The two compartments were dissolved in 70% nitric acid and submitted for AAS analysis to measure the Fe concentration. The percent binding calculated as Fe concentration of sediment/(Fe concentration of supernatant+Fe concentration of sediment)×100. In addition, the binding of nanoparticles to HA powder was measured in presence of different concentrations of NaCl ranging from 50 mM to 300 mM to prevent the unspecific bindings due to ionic interaction.

The effect of time on binding of SPION-ALN to HA was evaluated by incubating the sample with HA as explained above, followed by further sampling of the supernatant at 6 and 24 h. Furthermore, a sample of SPIONs conjugated with Tris instead of ALN is an additional negative control. Tris lacks the phosphonate groups of ALN, but similar to ALN, offers one primary amine for conjugation to carboxylic acid groups of modified SPIONs. Additionally, it has three hydroxyl groups at the other end, which are capable of binding to HA. The binding of bare SPIONs, SPION-ALN, and SPION-Tris were assessed in presence of various concentrations of rat serum.

Results

1. SPIONs Synthesis and Characterization

Figure 2:
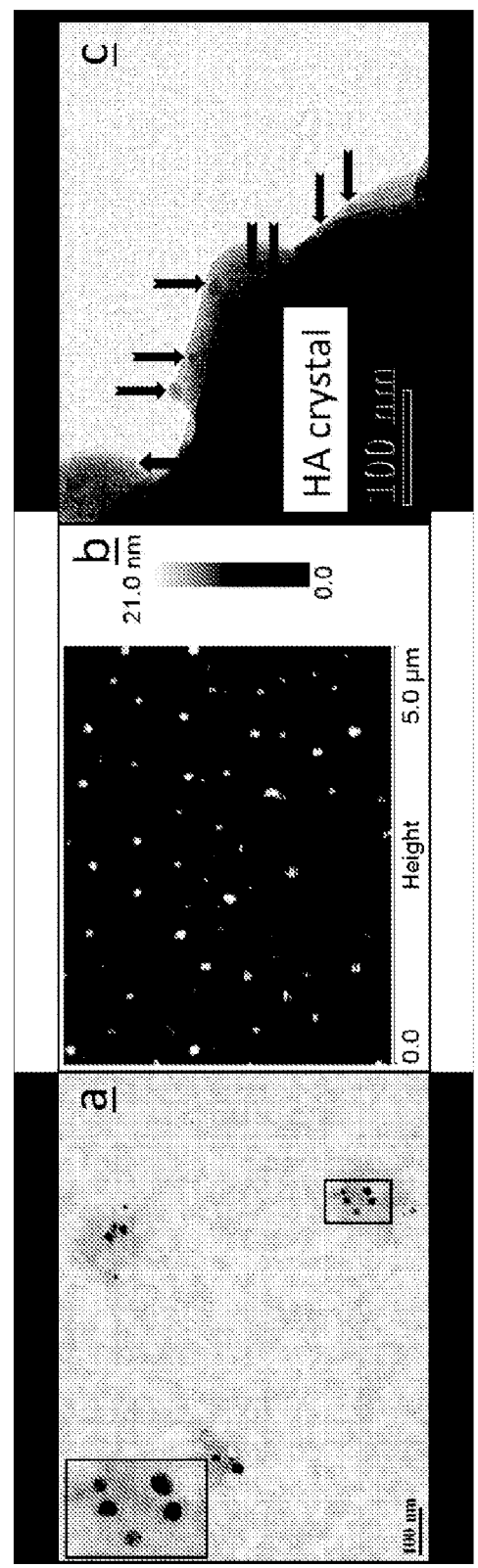
FIG. 2 shows TEM and AFM images of SPIONS. Panel (a) is a TEM image of bare SPIONs with spherical shapes and an average size of 16 nm. Panel (b) is a representative AFM image of SPIONs after ALN conjugation, showing an average size of 17 nm. Panel (c) depicts SPIONs-ALN targeted to an HA crystal after incubation for 2 h.

The size of SPIONs synthesized with the microemulsion technique ranged from 10 to 24 nm with the average of 16 nm, when 100 particles included in the measurement. AFM measurements on SPIONs-ALN showed the average size of 17 nm that correlated well with TEM results (FIG. 2). AFM image (FIG. 2b) was recorded in Magnetic Force Microscopy (MFM) mode using a magnetic tip, in other words it only recorded nanoparticles if they were magnetic. The changes in hydrodynamic size and zeta potential of nanoparticles were monitored at each step and in 3 different dispersants using DLS. The size of SPIONs in water and PB were measured 15 nm and 42 nm, respectively. While unchanged under TEM, SPIONs after conjugation with ALN experienced an increase in their hydrodynamic size both in water and PB and measured at 61 nm and 65 nm, respectively. The size of SPIONs coated with COOH (SPIONs-COOH) and SPIONs activated with EDC/NHS (SPIONs-Active) were both remained the same in water and PB and measured at 15 nm for SPIONs-COOH and 18 nm in case of SPIONs-Active. All nanoparticles except SPIONs-COOH and SPIONs-Active which slightly increased in their size, aggregated in PBS and accurate measurement was not accomplished.

Figure 3:
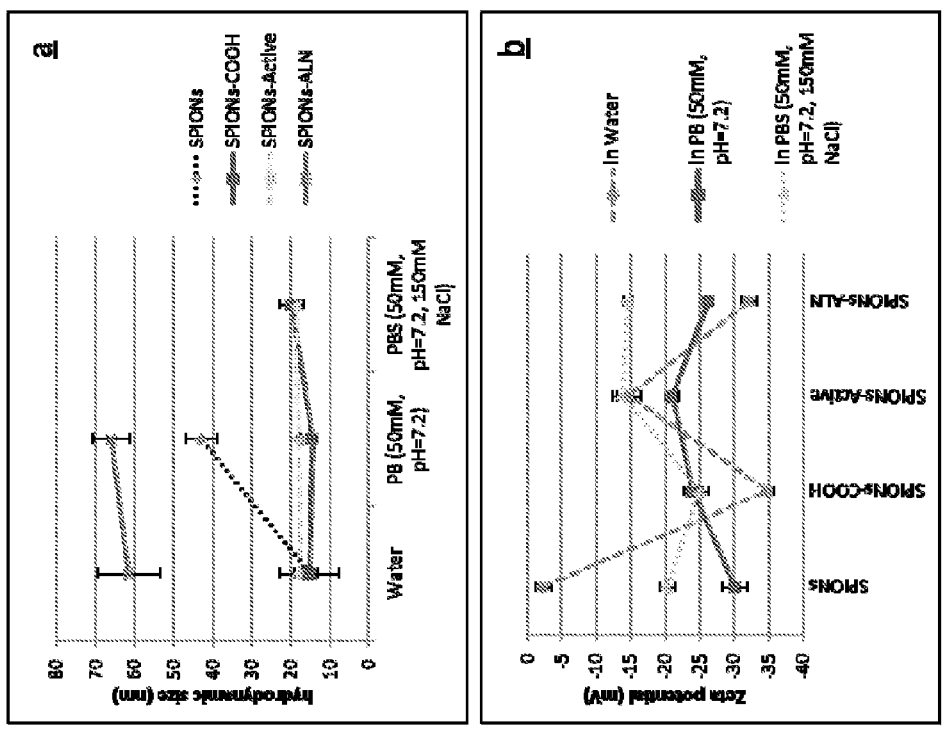
FIG. 3 shows DLS measurements. Panel (a) represents the hydrodynamic sizes of nanoparticles at each step in the conjugation process and in different dispersants. Panel (b) shows the zeta potentials of suspensions in different dispersants. Error bars in both panels represent standard deviation.

The zeta potential of nanoparticles dispersions was recorded in the same dispersant as in size measurement experiment (FIG. 3b) and served as one of the tools to conclude the formation of citric acid coating, activation and conjugation. The bare SPIONs in water and at pH=7 were slightly negatively charged (−2.3 mV) as result of being slightly above the point of zero charge. The same nanoparticles at pH=3 showed surface charge of +38.3±0.94 mV as a result protonation by water molecules. After coating the surface of bare SPIONs with citric acid, the surface charge of the nanoparticles changed from −2.3±1.19 mV to −34.9±0.81 mV. Activation of SPIONs-COOH with EDC/NHS increased the zeta potential to −14.7±1.61 mV. ALN molecule has two phosphonate groups in its structure and as a result, after conjugation to SPIONs-Active, the surface charge was lowered once more to −32.2±1.07 mV. The behavior of nanoparticles at each step in water, PB and PBS is presented in FIG. 3b.

2. Alendronate Conjugation

Figure 4:
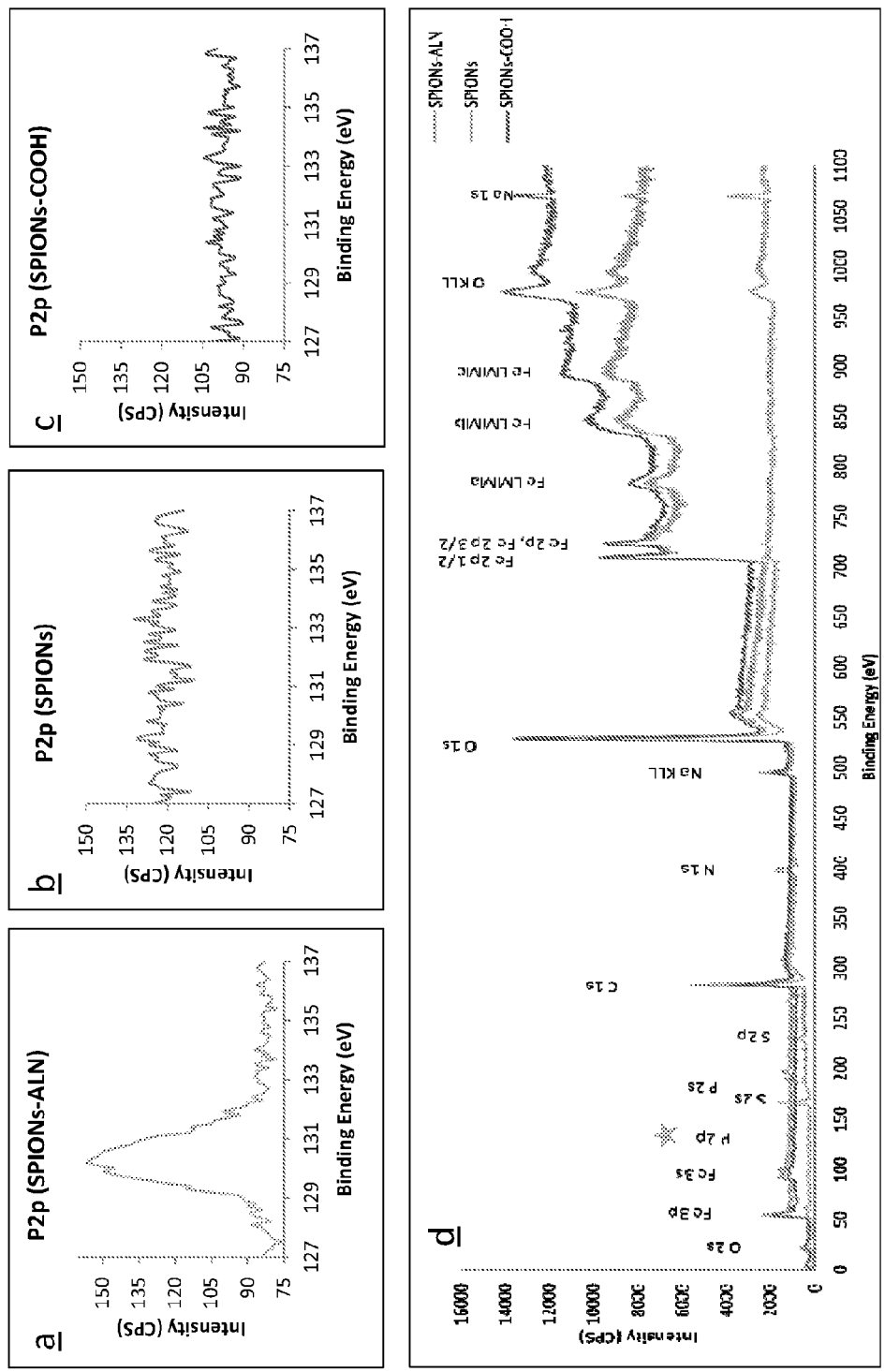
FIG. 4 shows XPS spectra. (a) The P2p peak of phosphorus was detected in SPIONs-ALN samples and interpreted as an indication of successful conjugation. (b) The absence of a phosphorus peak in the bare SPIONs sample is noted. (c) The absence of a phosphorus peak in the bare SPIONs-COOH sample is noted. Panel (d) is a survey spectrum showing all elements in the samples.
Figure 5:
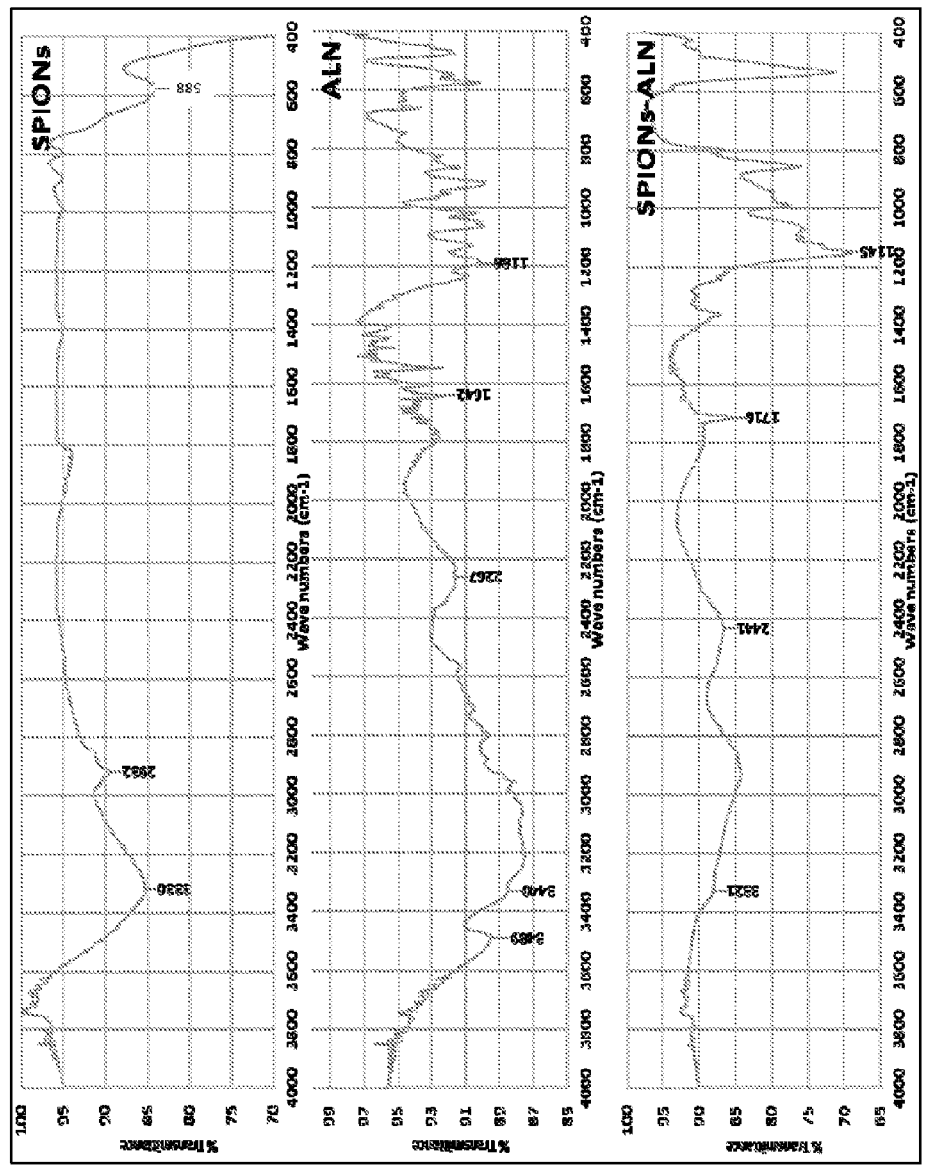
FIG. 5 shows FT-IR spectra. The presence of an amide peak at 1716 cm$^{-1}$ in the SPIONs-ALN sample as well as phosphonate peaks at 1145 cm$^{-1}$ (P=O) and 2441 cm$^{-1}$ (P—OH) indicate successful bisphosphonate conjugation.

As previously mentioned, ALN as a bisphosphonate has two phosphonate groups in its structure, in other words, each molecule of ALN has two phosphorous atoms. We used this as a means of determining the successful conjugation of ALN to SPIONs. Therefore, a sample of SPIONs-ALN was synthesized based on the abovementioned protocol with the only difference of using MES buffer (pH 6, 100 mM) instead of PB to provide a synthesis media free of phosphorous, giving us the confidence to relate any phosphorous peak to presence of ALN. After conjugation, the sample was dialyzed against MES buffer for 40 h with 4 changes of buffer, lyophilized and analyzed using XPS. The bare SPIONs showed no phosphorous peak as expected, however, the SPIONs-ALN showed the phosphorous peak which confirmed the successful conjugation (FIG. 4a). The low intensity of phosphorous peak was a result of efforts made to keep the concentration of ALN below therapeutic dose. Also, the absence of Fe peaks in SPIONs-ALN spectra is because of the surface coating of nanoparticle with citric acid. In order to more confidently associate any phosphorus peak on XPS, XPS analysis on a sample of SPIONs coated with citric acid was performed (FIG. 4c). Results confirmed no phosphorus peak; therefore it was concluded that the peak on SPIONs-ALN sample is associated with ALN molecule The FT-IR peak at 588 cm$^{-1}$ in bare SPIONs revealed that nanoparticles were mostly comprised of $Fe_3O_4$. The broad peak centered at 3330 cm$^{-1}$ is due to adsorbed molecular water as well as structural OH groups. The peak at 2932 cm$^{-1}$ was assigned to asymmetric $CH_2$ as a result of remained surfactants and washing solvents and could be removed by repeating the washing steps. Furthermore, FT-IR data was used to confirm the successful conjugation of ALN to SPIONs. ALN has a primary amine group and shows several characteristic bands including $NH_2$ stretch bands at 3340 cm$^{-1}$ and 3489 cm$^{-1}$, P—OH stretch at 2267 cm$^{-1}$ (broad), $NH_2$ bending at 1642 and P=O stretch at 1188 cm$^{-1}$. After amidation reaction, the peaks related to amine were disappeared and new peaks associated with amide structure appeared. The peak at 3321 cm$^{-1}$ was assigned to N—H stretch, 2441 cm$^{-1}$ to P—OH, 1716 cm$^{-1}$ to C=O amide and 1145 cm$^{-1}$ to P=O (FIG. 5). The new amide C=O peak and presence of phosphonate peaks in SPIONs-ALN supported the previously found results of XPS and DLS and confirmed the conjugation.

3. Bone Affinity Test

Figure 6:
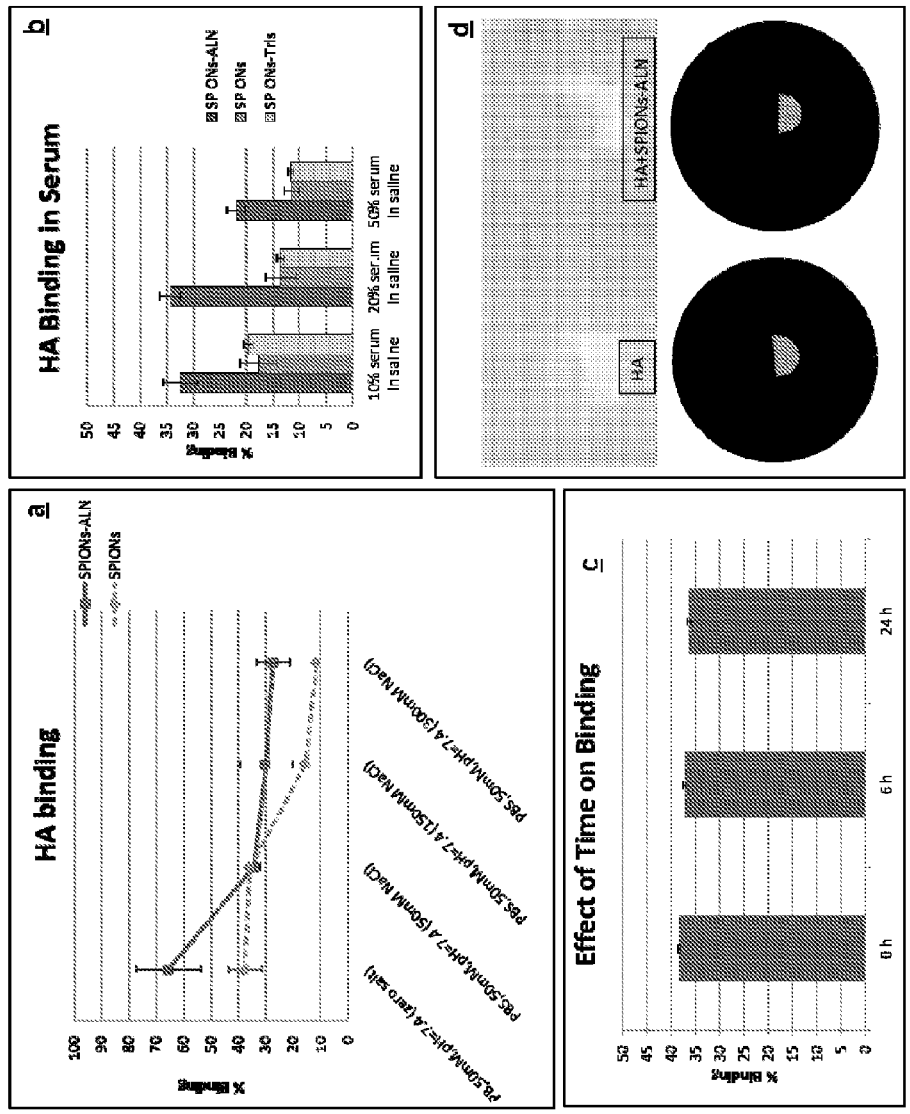
FIG. 6 shows binding assays of SPIONs-ALN to hydroxyapatite. Panel (a) shows that SPIONs-ALN was less susceptible to loss of binding by increasing the concentration of NaCl from 50 mM to 300 mM. Panel (b) shows HA binding in rat serum with significantly higher binding for SPIONs-ALN in all concentrations. Panel (c) is a graph representing negligible loss (<5%) of binding to HA over time for SPIONs-ALN. Panel (d) is the macroscopic image of HA powder (left) and HA powder incubated with SPIONs-ALN in PB (50 mM, pH=7.4) after washing process and their corresponding CT cross sectional slices. The error bars present standard deviation.

SPIONs-ALN was bound to HA powder at higher percentage in all solutions, compared to bare SPIONs (FIG. 6a). The highest percentage of binding for both samples was measured in PB at 65% and 37% binding for SPIONs-ALN and SPIONs, respectively. The percent binding was decreased by incremental addition of salt to the suspensions. This decrease in HA binding was more pronounced in case of SPIONs suggesting weak ionic bonds being responsible for the binding. 25% of SPIONs-ALN stayed bound to HA even at very high salt concentration of 300 mM NaCl compared to 11% for SPIONs. FIG. 6 shows the trend of nanoparticles binding to HA in different solutions. FIG. 6d, represents the macroscopic picture of SPIONs-ALN remained bound to HA powder after 7 steps of washing and the associated CT image. The CT image showed approximately 5% increase in the image intensity after incubation of HA powder with SPIONs-ALN due to higher atomic number of iron oxide nanoparticles.

In additional to measuring affinity of SPIONs-ALN toward hydroxyapatite (HA) in phosphate buffer with and without presence of salt, the binding test in incremental concentrations of rat serum was performed. The results showed significantly superior binding of SPIONs-ALN in all concentrations (FIG. 6b). Furthermore, the binding of SPIONs-ALN to HA were evaluated over time (FIG. 6c). After incubation for 24 hours, 95% of SPIONs-ALN nanoparticles remained bound to HA.

4. In Vitro and Ex Vivo MRI

Figure 7:
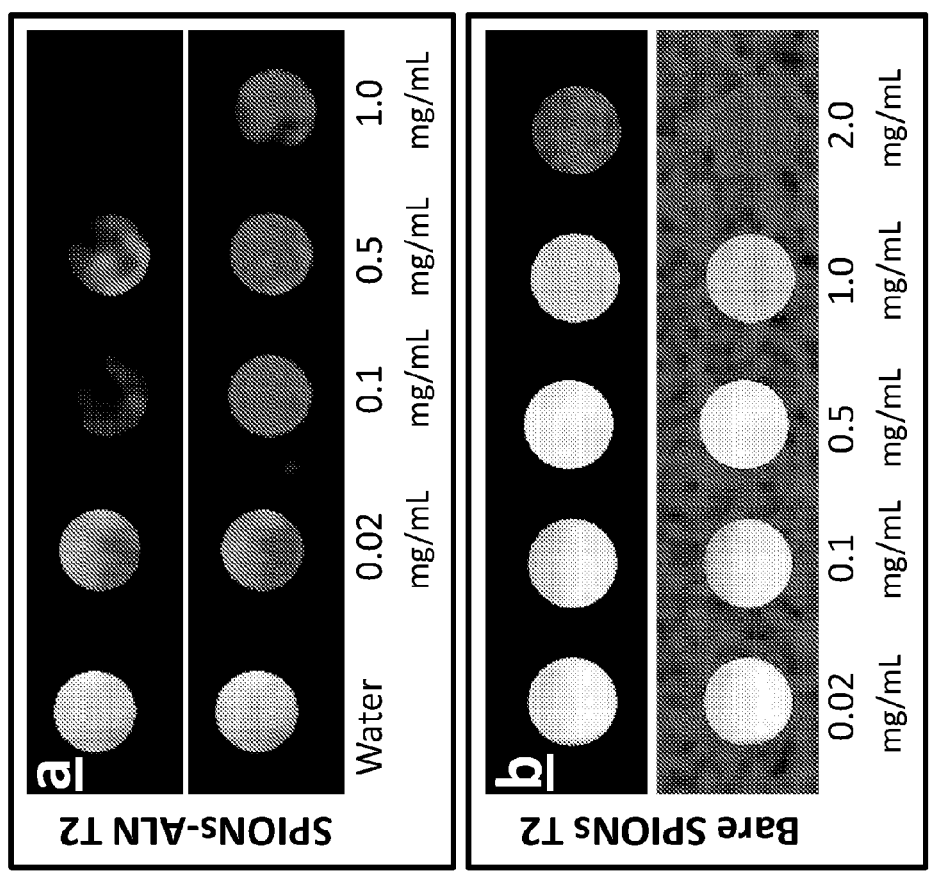
FIG. 7 shows in vitro MRI results. Panel (a) shows the signal loss of T2 MRI as a factor of increasing SPIONs-ALN concentration from 0 to 1.0 mg/mL. The corresponding colorized panel is also presented. Panel (b) shows the same effect from bare SPIONs.

Prior to in-vivo trial of SPIONs-ALN, a series of experiments to optimize MRI parameters were performed. Small tubes were filled with various concentrations of bare SPIONs and SPIONs-ALN and imaged with MRI. FIG. 7 shows MRI signal was decreased as the concentration of iron oxide nanoparticles increased. The optimal parameters for MRI were determined as T1 (TE/TR: 13/1250 ms) and intermediate T2-weighted (TE/TR: 25/2000 ms).

Figure 8:
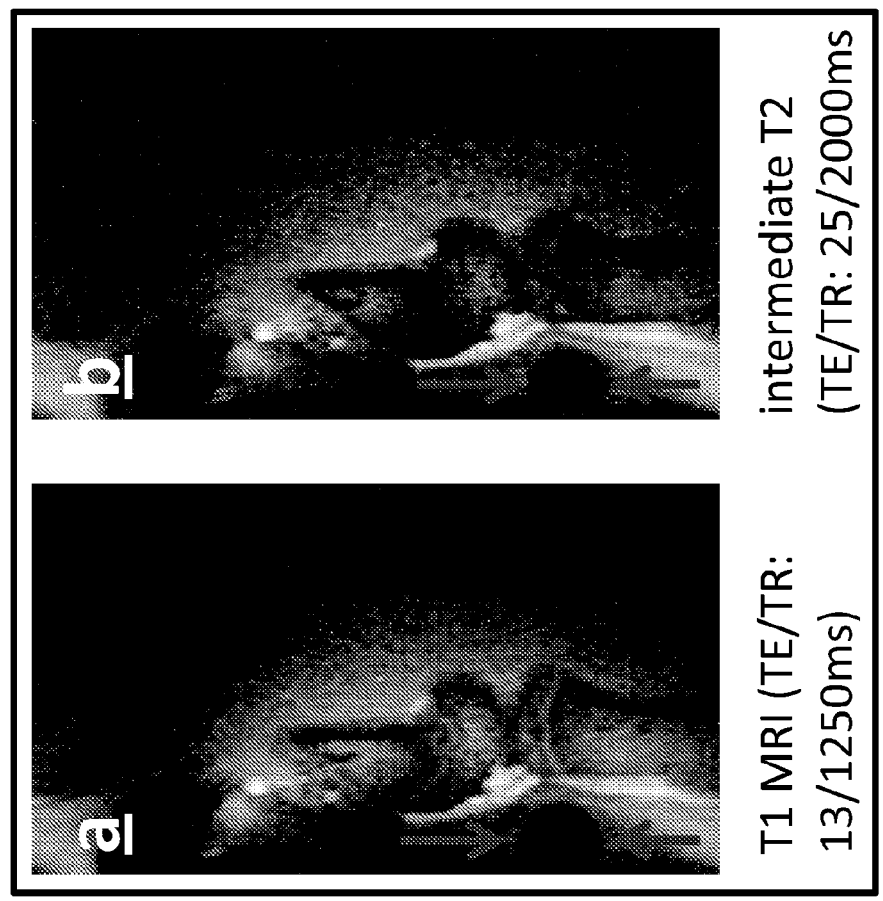
FIG. 8 shows ex vivo MRI results from a cadaveric rat knee joint injected subcutaneously with SPIONs-ALN by (a) T1 MRI and (b) Intermediate T2 MRI.

In addition, a volume of 250 μL SPIONs-ALN (conc. 1 mg/mL) was injected subcutaneously to a cadaveric sample of a rat and MRI with the abovementioned parameters were performed. FIG. 8 shows the visualization of nanoparticles in the injected location both on T1 and T2 MRI.

5. In Vivo MRI

The in-vivo efficacy of SPIONs-ALN to target and detect bone turnover was evaluated in a model of post-traumatic OA (PTOA). PTOA was induced in rats surgically by removing medial meniscus and transecting ACL and MCL ligaments. The lateral side of the joint was considered as control. Nanoparticles were administered intravenously to rats (n=3) 3 weeks after the surgery (i.e. early OA) at dose of 2.7 mg/Kg Fe (48 μmol/Kg Fe). T1 (TE/TR: 13/1250 ms) and intermediate T2-weighted (TE/TR: 25/2000 ms) MRI were acquired at 20 min and 3 h after injection, utilizing a 9.4 T in-vivo micro-MRI. After MRI imaging, animals were euthanized and samples were collected for general histological evaluation and detection of iron nanoparticles.

Figure 9:
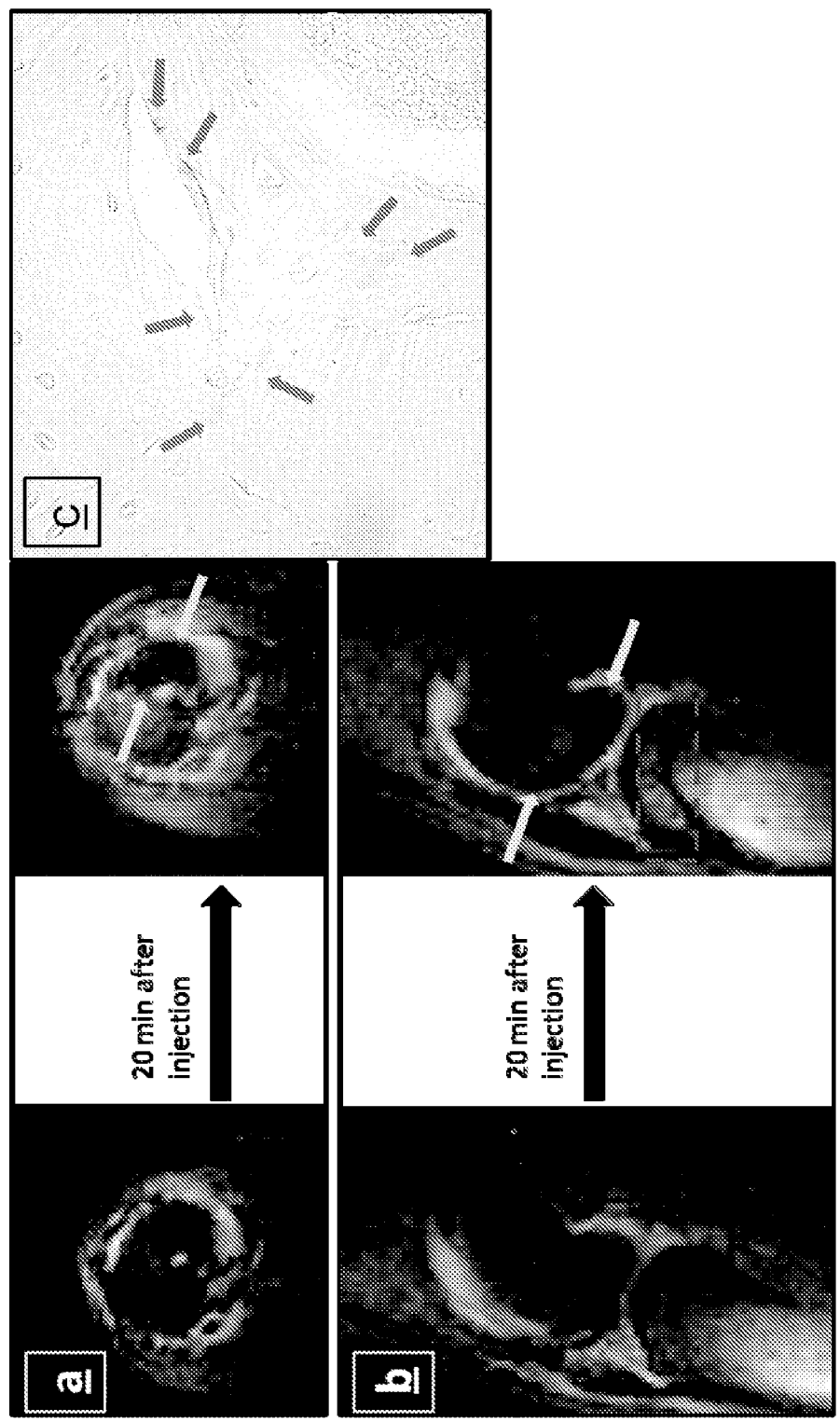
FIG. 9 shows intermediate T2-weighted fat-suppressed MRI. Panel (a) shows a transverse plane showing 'negative enhancement' of the joint (medial) with dark bands developing after SPIONs-ALN injection. Panel (b) shows a sagittal plane showing 'negative enhancement' at femoral trochlear and condylar subchondral bone (arrows) as well as the growth plate (red box). Panel (c) shows Prussian blue staining of the tibia showing iron deposition at subchondral bone (arrows).

In-vivo MRI revealed 'negative enhancement' at regions of active remodeling as early as 20 min following SPIONs-ALN injection, definable as dark hypointense band of decreased signal on T1 and T2 weighted MR sequences (FIG. 9). The areas of greatest 'negative enhancement' included the growth plates (which are open and active sites of bone turnover in rats throughout life), the tibial and femoral subchondral bone, and the femoral trochlear groove, which is a region known to later develop osteophytes in this animal model (FIGS. 9a and b). Enhancement remained present for at least 3 hours after injection.

Histological evaluation of the samples after decalcification and staining with Prussian Blue (FIG. 9c) revealed accumulation of iron at subchondral bone in samples injected with SPIONs-ALN, but not bare SPIONs. Since decalcification process in order to section histological slides also results in removal of inorganic elements other than calcium, the staining is fairly faint.

Figure 10:
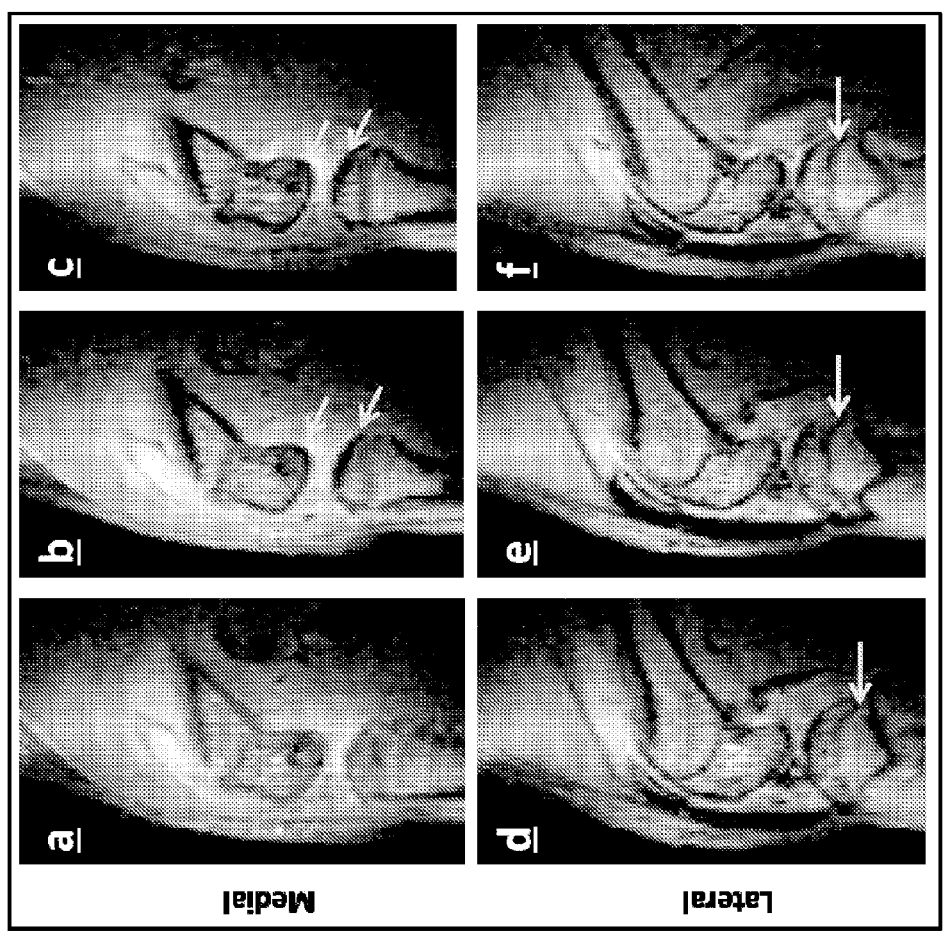
FIG. 10 shows T1-weighted MRI from the medial (operated side) and lateral (control) sides of the same joint before (a, d), 20 minutes (b, e), and 3 hours (c, 0 after SPIONs-ALN injection revealed negative enhancement at growth plates and subchondral bones both in femur and tibia (arrows) for medial joint, whereas at lateral compartment only growth plates were sufficiently enhanced, meaning no excessive bone turnover in the lateral joint.

FIG. 10 shows T1-weighted MRI from the medial (operated side) and lateral (control) sides of the same joint before (a, d), 20 minutes (b, e), and 3 hours (c, 0 after SPIONs-ALN injection revealed negative enhancement at growth plates and subchondral bones both in femur and tibia (arrows) for medial joint, whereas at lateral compartment only growth plates were sufficiently enhanced, which means there was no excessive bone turnover in the lateral joint.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. An iron nanoparticle comprising a superparamagnetic iron oxide nanoparticle with a linker comprising two or more carboxylate groups coated on the surface of the nanoparticle and a bone targeting moiety covalently bonded to the linker via a carboxylate group on the linker, wherein the composition is neutral or a pharmaceutically acceptable salt or ester thereof.

2. The nanoparticle of claim 1, wherein the linker comprises citric acid.

3. The nanoparticle of claim 1, wherein the bone targeting moiety comprises a bisphosphonate containing compound, wherein the bisphosphonate containing compound comprises formula I

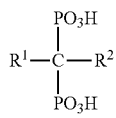

wherein $R^1$ and $R^2$ are, independently, hydrogen, a hydroxyl group, an alkyl group, an alkylene group, an amine group, a thiol group, an aryl group, or any combination thereof, or the pharmaceutically salt or ester thereof, and wherein $R^1$ or $R^2$ is covalently attached to the linker.

4. The nanoparticle of claim 3, wherein $R^1$ is hydroxyl and $R^2$ is an alkyl group terminated by a primary amine.

5. The nanoparticle of claim 1, wherein the bone targeting moiety comprises an amino bisphosphonate compound.

6. The nanoparticle of claim 1, wherein the bone targeting moiety comprises a residue of etidronic acid, clodronic acid, tiludronic acid, pamidronic acid, neridronic acid, olpadronic acid, alendronic acid, ibandronic acid, zolendronic acid, risedronic acid, or a combination thereof.

7. The nanoparticle of claim 1, wherein the bone targeting moiety is a residue of [4-amino-1-hydroxy-1-(hydroxy-oxido-phosphoryl)-butyl]phosphonic acid or a pharmaceutically-acceptable salt or ester thereof.

8. The nanoparticle of claim 1, wherein the linker is citric acid and wherein the bone targeting moiety is a residue of [4-amino-1-hydroxy-1-(hydroxy-oxido-phosphoryl)-butyl] phosphonic acid or a pharmaceutically-acceptable salt or ester thereof.

9. A method of making an iron nanoparticle comprising:
   a. coating a superparamagnetic iron oxide nanoparticle with a linker comprising two or more carboxylate groups to form a first nanoparticle, wherein the linker comprises at least one unreacted carboxylate group;
   b. reacting the first nanoparticle with a bisphosphonate compound, wherein the bisphosphonate compound has a carboxylate-reactive group to form a covalent bond with the linker and produce the iron nanoparticle.

10. The method of claim 9, wherein the linker comprises citric acid.

11. The method of claim 9, wherein the ratio of nanoparticle to linker in step (a) is from 1:1 to 10:1.

12. The method of claim 9, wherein step (a) comprises reacting the nanoparticle and the linker for from 10 minutes to 8 hours at room temperature.

13. The method of claim 9, wherein prior to step (b) purifying the first particle by magnetic separation.

14. A method of imaging a bone in a subject comprising:
   a. administering the composition of claim 1 to a subject; and
   b. imaging the bone by magnetic resonance imaging.

15. The method of claim 14, wherein the composition is administered to the subject intravenously.

16. The method of claim 14, wherein the composition is injected directly into a joint of the subject.

17. The method of claim 14, wherein the subject has been diagnosed with a metabolic bone disorder.

18. The method of claim 17, wherein the metabolic bone disorder is Paget's disease, osteolytic tumors, rheumatoid arthritis, psoriatic arthritis, ankylosing spondylitis, osteoarthritis, hypercalcemia, osteopenia, or any combination thereof.

19. The method of claim 14, wherein the subject is a mammal.

20. The method of claim 14, wherein the subject is a human.

21. The nanoparticle of claim 1, wherein the linker has two to five carboxylate groups.

22. The nanoparticle of claim 1, wherein the linker comprises a tricarboxylic acid.

23. An iron nanoparticle produced by the method of claim 9.

* * * * *